(12) United States Patent
Clardy

(10) Patent No.: US 11,260,141 B1
(45) Date of Patent: Mar. 1, 2022

(54) DEODORIZING ATTACHMENT FOR A FAN

(71) Applicant: Yalonda Clardy, Lenexa, KS (US)

(72) Inventor: Yalonda Clardy, Lenexa, KS (US)

( * ) Notice: Subject to any disclaimer, the term of this patent is extended or adjusted under 35 U.S.C. 154(b) by 0 days.

(21) Appl. No.: 17/029,776

(22) Filed: Sep. 23, 2020

(51) Int. Cl.
*A61L 9/12* (2006.01)
*A61L 9/04* (2006.01)

(52) U.S. Cl.
CPC .............. *A61L 9/042* (2013.01); *A61L 9/048* (2013.01); *A61L 9/122* (2013.01); *A61L 2209/133* (2013.01); *A61L 2209/15* (2013.01)

(58) Field of Classification Search
None
See application file for complete search history.

(56) References Cited

U.S. PATENT DOCUMENTS

| | | | |
|---|---|---|---|
| 3,844,478 A * | 10/1974 | Davis | A61L 9/12 239/57 |
| 5,935,526 A * | 8/1999 | Moore | A61L 9/122 422/124 |
| 6,241,219 B1 * | 6/2001 | Logan | A61L 9/122 239/56 |
| 7,622,073 B2 | 11/2009 | Schramm et al. | |
| 8,097,214 B2 | 1/2012 | Wood | |
| 8,709,347 B2 | 4/2014 | Lackey et al. | |
| 10,207,017 B2 | 2/2019 | Orito et al. | |
| 10,426,861 B2 | 10/2019 | Furner et al. | |
| 2003/0012680 A1 * | 1/2003 | Balsys | B32B 5/16 422/5 |
| 2013/0093108 A1 * | 4/2013 | Scolari | A61L 9/122 261/146 |

OTHER PUBLICATIONS

Mini Handheld Fan,GUSGU Portable Personal Fan with Removable Aroma Diffuser Features Oscillating USB Rechargeable Battery Operated Mini Fan for Travel/Workout/Offices/Sleep(5 Speed Adjustable). Product Listing [online]. © 1996-2020, Amazon.com, Inc. [retrieved on Mar. 13, 2020]. Retrieved from the Internet: <URL: https://www.amazon.com/GUSGU-Removable-Oscillating-Rechargeable-Adjustable/dp/B07RDB32T1>.

ScentAir Essence Machine. Product Listing [online]. © 2019-2020 ScentAir [retrieved on Mar. 13, 2020]. Retrieved from the Internet: <URL: https://scentairhome.com/Product/ScentAir-Essence?gclid=Cj0KCQjw0pfzBRCOARIsANi0g0vNzOAi1OyaF6SEnc3gdR1P_DANLCidmlHDVQy8nveElp3i3fqqgzoaAkwQEALw_wcB>.

* cited by examiner

*Primary Examiner* — Jelitza M Perez
(74) *Attorney, Agent, or Firm* — Cramer Patent & Design PLLC; Aaron R. Cramer

(57) ABSTRACT

A deodorizing attachment for a fan includes a plate having an adhesive backing and a plurality of open-faced cups being disposed upon a face opposite the backing. Each cup has a mesh cover with each cup being configured to removably secure a unit of an air freshener.

14 Claims, 5 Drawing Sheets

DEODORIZING ATTACHMENT FOR A FAN

RELATED APPLICATIONS

None.

FIELD OF THE INVENTION

The present invention relates to an air deodorizer and more specifically to a deodorizing attachment for a fan.

BACKGROUND OF THE INVENTION

The battle to keep a room clean and fresh smelling is an everlasting one. Stale odors, poor circulation, tobacco smoke, food odors and the like all combine to assault the olfactory senses of anyone entering the room. Various means to combat these odors have been invented. They include the use of aerosol sprays, solid room deodorizers, electric room deodorizers, and the like. A common problem with all of these systems is that the freshening smell is overpowering at first, and then the aroma quickly diminishes with time.

Another problem area is that the freshening aroma is not evenly distributed around the room or area and is only concentrated in the area where it was released. The final problem with all of these systems is that the user must remember to use them and use them on a consistent and regular basis. Accordingly, the need has arisen for the distribution of air fragrances by automatic and unattended means. The development of the deodorizing device for fans fulfills this need.

SUMMARY OF THE INVENTION

The principles of the present invention provide for a deodorizing device which comprises a base having an outer face and a bottom, a plurality of mesh holders with each having a circular mesh sidewall and a hinged mesh lid. Each of the hinged mesh lids are attached to its respective circular mesh sidewall. The deodorizing device also comprises a solid deodorizer contained within each of the mesh holders.

The deodorizing device may further comprise a plurality of double-sided foam tape which is disposed on the bottom of the base to attach the deodorizing device to a surface. The base may be circular and may be six inches in diameter. Each of the hinged mesh lids may be attached to the respective circular mesh sidewall with a hinge and a snap clasp and each of the hinged mesh lids may be opened to replace one of the dissolved solid deodorizers.

The mesh holders may be made of plastic which may be an injection molded plastic. There may be seven mesh holders. The solid deodorizer may be made of a wax that dissolves in air or a gel base that dissolves in air. The mesh holders may contain a plurality of the solid deodorizers. The solid deodorizer may be 0.835 inches in diameter and/or may be one-quarter inch in thickness. The deodorizing device may be disposed on a ceiling fan, a box fan, a pedestal fan, a window fan, or an oscillating fan.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
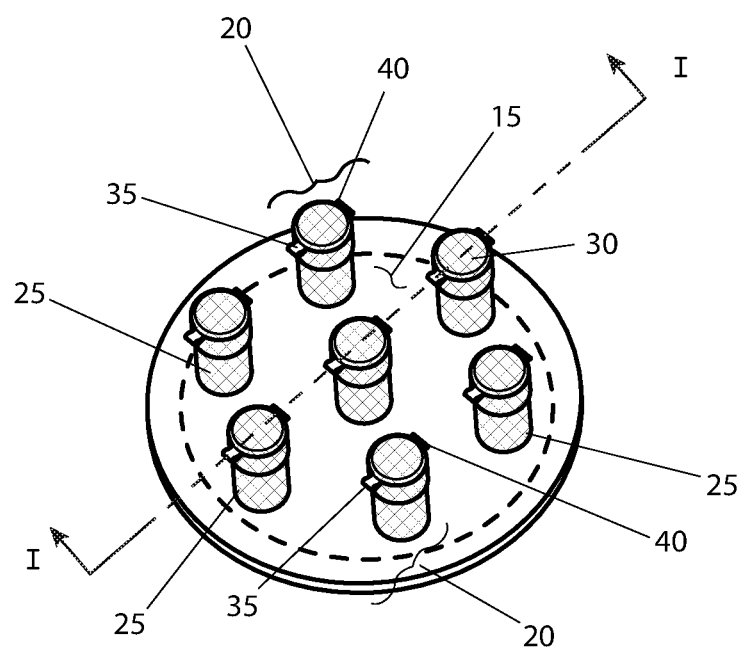
FIG. 1 is a perspective view of a deodorizing device, according to the preferred embodiment of the present invention.

DESCRIPTIVE KEY 10 deodorizing device
15 circular base
20 mesh holder
25 circular mesh sidewall
30 hinged mesh lid
35 hinge
40 snap clasp
45 solid deodorizer
50 double-sided foam tape
55 peel-off layer
60 air flow
65 ceiling fan
70 ceiling fan blade
75 air motion
80 occupied space
85 box fan
90 box fan blade

DESCRIPTION OF THE PREFERRED EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Referring now to FIG. 1, a perspective view of the deodorizing device 10, according to the preferred embodiment of the present invention is disclosed. The deodorizing device 10 (herein also described as the "device") 10, provides for the automatic deployment and dispersement of solid room deodorizing tablets 45 using the air moving feature of room fans 65, 85. The device 10 includes of a circular base 15. The overall diameter of the circular base 15 may vary with each specific model with a typical diameter being approximately six inches (6 in.). However, the exact size of the circular base 15 is not intended to be a limiting factor of the present invention. The outer face of the circular base 15 is provided with multiple mesh holders 20 each having a circular mesh sidewall 25 and a hinged mesh lid 30. Each hinged mesh lid 30 is attached to its respective circular mesh sidewall 25 with the aid of a hinge 35 and snap clasp 40 as shown. The exact quantity of mesh holders 20 may vary, dependent on the size of the circular base 15. A typical sized circular base 15 would contain approximately seven (7) mesh holders 20 as depicted in FIG. 1. The exact quantity of mesh holders 20 is not intended to be a limiting factor of the present invention. It is envisioned that the circular base 15 as well as the multiple mesh holders 20 are made of a unitary plastic assembly in an injection molding process.

Figure 2:
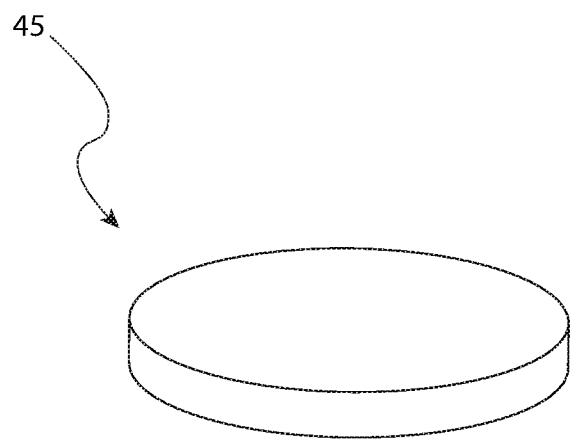
FIG. 2 is a perspective view of the solid deodorizer as used with deodorizing device, according to the preferred embodiment of the present invention.

Referring next to FIG. 2, a perspective view of the solid deodorizer 45 as used with the device 10, according to the preferred embodiment of the present invention is depicted. The solid deodorizer 45 is envisioned to be made of a wax or encased gel base that dissolves in air over time in a manner similar to that of conventional solid room deodorizing devices. It is envisioned that the solid deodorizer 45 would be made in a wide variety of fragrances to suit the personal tastes of all users. The solid deodorizer 45 is individually placed within each mesh holders 20 (as shown in FIG. 1) and would be periodically replaced when completely dissolved. The approximate size of the solid deodorizer 45 would be 0.835 inches in diameter and approximately one-quarter inch (¼ in.) in thickness.

Figure 3:
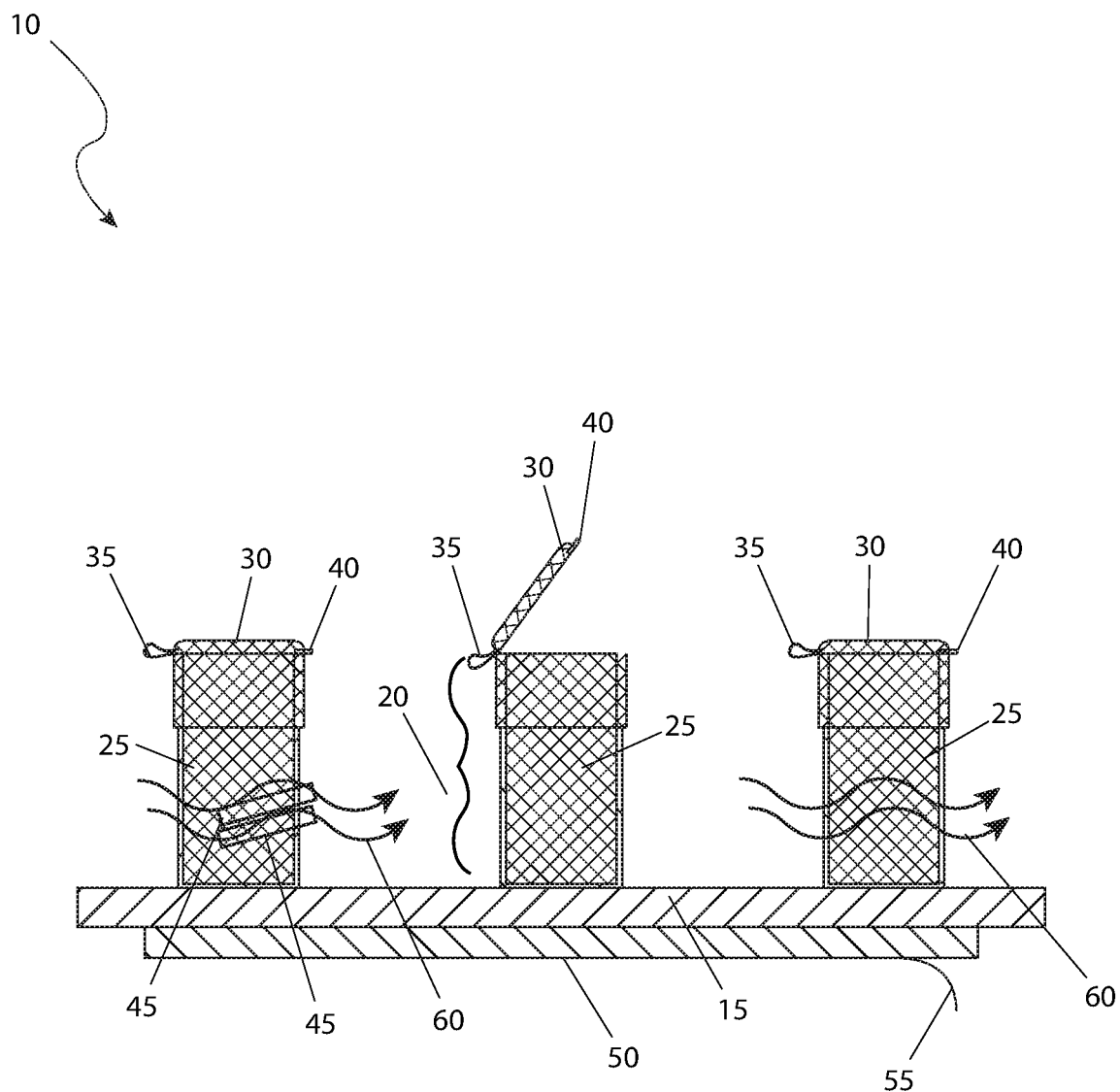
FIG. 3 is a sectional view of the deodorizing device, as seen along a Line I-I, as shown in FIG. 1, according to the preferred embodiment of the present invention.

Referring now to FIG. 3, a sectional view of the device 10, as seen along a line I-I, as shown in FIG. 1, according to the preferred embodiment of the present invention is shown. Three (3) of the multiple mesh holders 20 are shown affixed to the circular base 15. The left mesh holders 20 as shown contains two (2) solid deodorizer 45 for purposes of illustration. The middle mesh holders 20 is shown with an open hinged mesh lid 30, as would be seen during replacement of solid deodorizer 45, for purposes of illustration. The right mesh holders 20 is shown with no solid deodorizer 45 inside as would occur when the solid deodorizer 45 have completely evaporated and are in need of replacement, for purposes of illustration. It is noted that the presence or lack of presence of any solid deodorizer 45 does not impact the operation of any fan as the circular base 15 is attached to. The attachment process is facilitated with the use of double-sided foam tape 50 on the bottom of the circular base 15. A peel-off layer 55 is removed by the end user when affixing the device 10 to a fan as will be described below. This view also provides clarification of the hinge 35 and the snap clasp 40 and its ability to secure the hinged mesh lid 30 to the circular mesh sidewall 25. The open nature of the circular mesh sidewall 25 and the hinged mesh lid 30 allow for easy air flow 60 through the interior of the mesh holders 20 allowing the fragrance of the solid deodorizer 45 to be carried throughout the space in which the device 10 is utilized.

Figure 4:
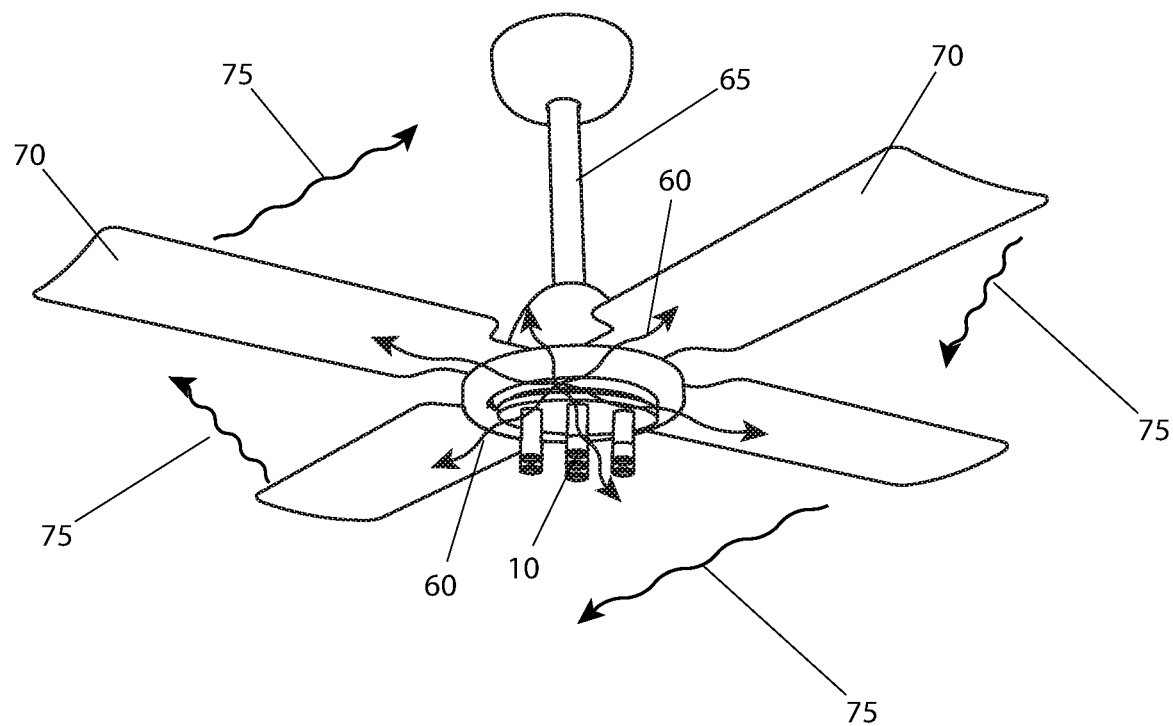
FIG. 4 is a perspective view of the deodorizing device, shown in a utilized state on a ceiling fan. according to the preferred embodiment of the present invention; and, FIG. 5 is a perspective view of the deodorizing device, shown in a utilized state on a box fan, according to the preferred embodiment of the present invention.

Referring next to FIG. 4, a perspective view of the device 10, shown in a utilized state on a ceiling fan 65. according to the preferred embodiment of the present invention is disclosed. The ceiling fan 65 is of a conventional common design and is configured and operations in a typical manner. The ceiling fan blades 70 create air motion 75 under use. The air motion 75 creates air flow 60 through the mesh holders 20 (as shown in FIG. 1 and FIG. 3) of the deodorizing device for fans 10, leading to a dispersion of the fragrance of the solid deodorizer 45 being distributed about the occupied space 80. The air motion 75 ensures a constant and greater dispersion of the fragrance than without the use of the ceiling fan 65. This greater dispersion ensures a move even and effective masking of unwanted odors in the occupied space 80, leading to a more pleasant olfactory experience.

Figure 5:
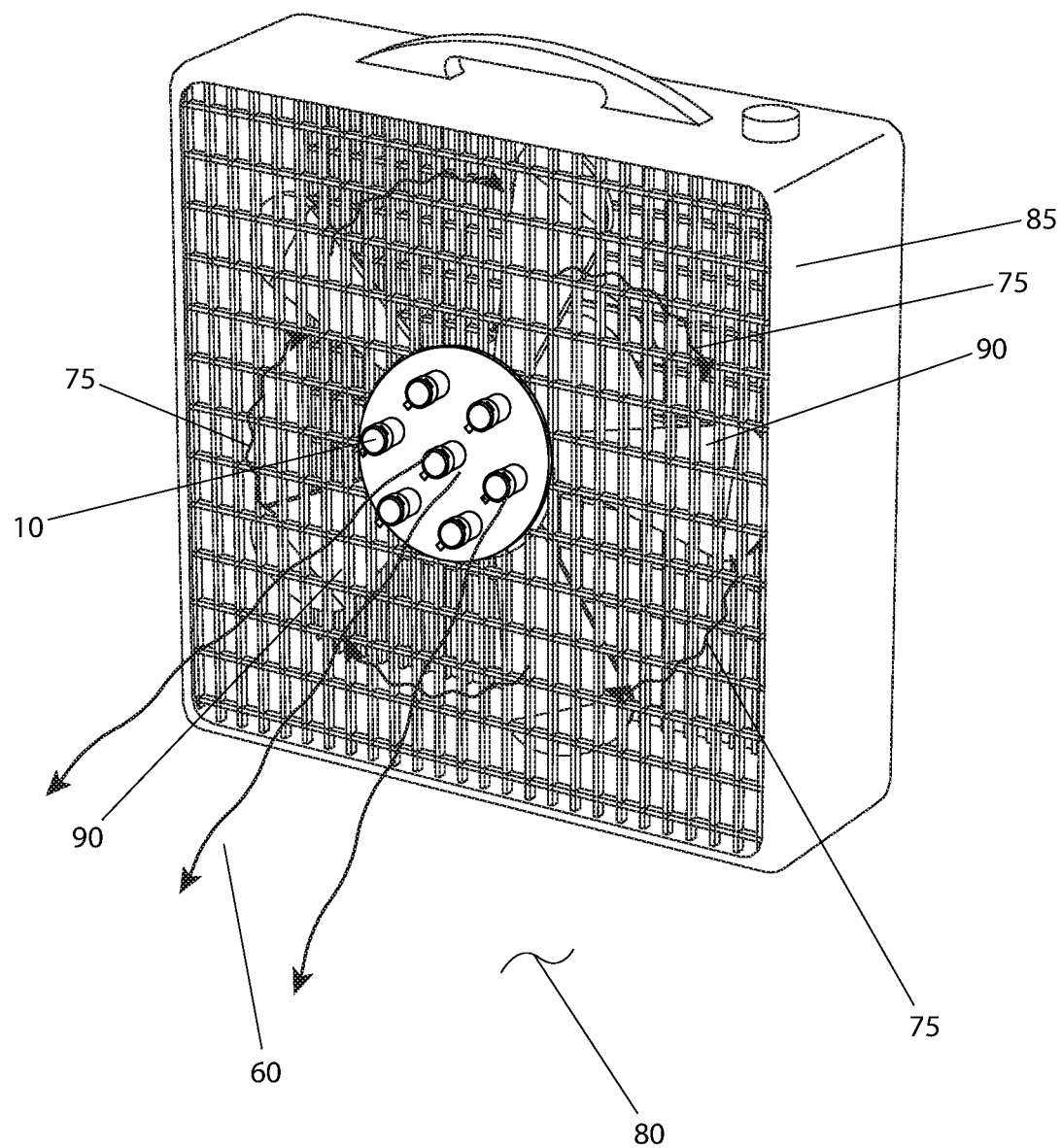

Referring now to FIG. 5, a perspective view of the device 10, shown in a utilized state on a box fan 85. according to the preferred embodiment of the present invention is depicted. The box fan 85 is of a conventional common design and is configured and operations in a typical manner. The box fan blades 90 create air motion 75 under use. The air motion 75 creates air flow 60 through the mesh holders 20 (as shown in FIG. 1 and FIG. 3) of the deodorizing device for fans 10, leading to a dispersion of the fragrance of the solid deodorizer 45 being distributed about the occupied space 80. The air motion 75 ensures a constant and greater dispersion of the fragrance than without the use of the ceiling fan 65. This greater dispersion ensures a move even and effective masking of unwanted odors in the occupied space 80, leading to a more pleasant olfactory experience.

It is noted that other types of fans other than the ceiling fan 65 as shown in FIG. 4 and the box fan 85 (as shown in FIG. 5) may be utilized with the device 10. Such fans include, but are not limited to: desk fans, pedestal fans, window fans, oscillating fans, and the like. As such, the use of the device 10 with any particular type or style of fan shall not be a limiting factor of the present invention.

2. Operation of the Preferred Embodiment

The preferred embodiment of the present invention can be utilized by the common user in a simple and effortless manner with little or no training. It is envisioned that the device 10 would be constructed in general accordance with FIG. 1 through FIG. 5. The user would procure the device 10 from conventional procurement channels such as hardware stores, home improvement stores, discount stores, department stores, mail order and internet supply houses and the like. Special attention would be paid to the overall size of the device 10 (diameter of the circular base 15), number of mesh holders 20, and color of the device 10, so as to match or contrast with the color of the fan upon which it is used.

After procurement and prior to utilization, the device 10 would be prepared in the following manner: the peel-off layer 55 would be removed from the double-sided foam tape 50 and the device 10 affixed to either a ceiling fan 65, a box fan 85, or similar type of fan, the hinged mesh lid 30 of the circular mesh sidewall 25 would be opened by manipulation of the snap clasp 40 and the hinge 35; multiple solid deodorizer 45 of the user's fragrance choice would be inserted into the mesh holders 20 and the hinged mesh lid 30 closed. At this point in time, the device 10 is ready for utilization.

During utilization of the device 10, the following procedure would be initiated: the ceiling fan 65, the box fan 85, or other type of fan upon which the device 10 is utilized would be energized and operated in the typical manner in a transparent manner to the unknowing user. As the ceiling fan blades 70, the box fan blades 90, or other fan blades move, they create air motion 75 which passes through the circular mesh sidewall 25 and the hinged mesh lid 30 of the mesh holders 20 and over the solid deodorizer 45 contained within; the resultant fragrance is then distributed by the subsequent occupied space 80 throughout the occupied space 80 creating a pleasant olfactory experience.

The usage described above continues until the solid deodorizer 45 are completely absorbed or evaporated; at such time, the solid deodorizer 45 are replaced following the initial placement procedure as described above. This general process of installation, usage, evaporation and replacement, continues in a circular and repetitive manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A deodorizing device, comprising:
 a circular base having an outer face and a bottom;
 a plurality of mesh holders each having a circular mesh sidewall and a hinged mesh lid, each of the hinged mesh lids are attached to its respective circular mesh sidewall;
 a solid deodorizer contained within each of the mesh holders; and
 a plurality of double-sided foam tape disposed on the bottom of the circular base to attach the deodorizing device to a surface;
 wherein each of the hinged mesh lids are attached to the respective circular mesh sidewall with a hinge and a snap clasp;
 wherein each of the hinged mesh lids are opened to replace one of the dissolved solid deodorizers;
 wherein each of the mesh holders contain a plurality of the solid deodorizers; and
 wherein each of the mesh holders are affixed to the circular base and extend perpendicularly from the circular base.

2. The deodorizing device according to claim 1, wherein the circular base is 6 inches in diameter.

3. The deodorizing device according to claim 1, wherein the mesh holders are made of plastic.

4. The deodorizing device according to claim 3, wherein the mesh holders are made of injection molded plastic.

5. The deodorizing device according to claim 1, wherein there are seven mesh holders.

6. The deodorizing device according to claim 1, wherein solid deodorizer is made of a wax that dissolves in air.

7. The deodorizing device according to claim 1, wherein solid deodorizer is made of a gel base that dissolves in air.

8. The deodorizing device according to claim 1, wherein the solid deodorizer is 0.835 inches in diameter.

9. The deodorizing device according to claim 1, wherein the solid deodorizer is one-quarter inch in thickness.

10. The deodorizing device according to claim 1, wherein the deodorizing device is disposed on a ceiling fan.

11. The deodorizing device according to claim 1, wherein the deodorizing device is disposed on a box fan.

12. The deodorizing device according to claim 1, wherein the deodorizing device is disposed on a pedestal fan.

13. The deodorizing device according to claim 1, wherein the deodorizing device is disposed on a window fan.

14. The deodorizing device according to claim 1, wherein the deodorizing device is disposed on an oscillating fan.

* * * * *